United States Patent [19]

Sehgal et al.

[11] Patent Number: 5,066,493
[45] Date of Patent: Nov. 19, 1991

[54] RAPAMYCIN IN TREATMENT OF TUMORS

[75] Inventors: Surendra N. Sehgal, Princeton, N.J.; Claude Vezina, Oka, Canada

[73] Assignee: American Home Products Corporation, New York, N.Y.

[21] Appl. No.: 682,813

[22] Filed: Apr. 9, 1991

Related U.S. Application Data

[60] Continuation-in-part of Ser. No. 391,334, Aug. 9, 1989, abandoned, which is a division of Ser. No. 592,193, Mar. 22, 1984, Pat. No. 4,885,171, which is a continuation of Ser. No. 126,276, Mar. 3, 1980, abandoned, which is a continuation of Ser. No. 957,626, Nov. 3, 1978, abandoned.

[51] Int. Cl.$^5$ .................. H61K 31/66; H61K 31/505; H61K 31/415; H61K 35/74
[52] U.S. Cl. .................................... 424/122; 514/110; 514/274; 514/291
[58] Field of Search ...................... 514/291, 110, 274; 424/122

[56] References Cited

U.S. PATENT DOCUMENTS 3,929,992 12/1975 Sehgal et al. .................. 424/122

OTHER PUBLICATIONS

C. P. Eng et al., J. Antibiotics, 37, No. 10, 1231–1237 (1984).
C. Vezina et al., J. Antibiotics, 28, 721 (1975).
S. N. Sehgal et al., J. Antibiotics, 28, 727 (1975).

Primary Examiner—Jerome D. Goldberg
Attorney, Agent, or Firm—Walter Patton

[57] ABSTRACT

Methods of using rapamycin in the treatment of cancers or tumors are disclosed.

6 Claims, No Drawings

RAPAMYCIN IN TREATMENT OF TUMORS

BACKGROUND OF THE INVENTION

This is a continuation-in-part application of co-pending application Ser. No. 07/391,334, filed Aug. 9, 1989, now abandoned, which in turn is a divisional application of co-pending application Ser. No. 06/592,193, filed on Mar. 22, 1984, now issued as U.S. Pat. No. 4,885,171, on Dec. 5, 1989, which in turn is a continuation application of co-pending application Ser. No. 06/126,276, filed on Mar. 3, 1980, now abandoned, which in turn is a continuation application of co-pending application Ser. No. 05/957,626, filed Nov. 3, 1978, now abandoned.

1. Field of the Invention

This invention relates to the use of rapamycin as an anti-cancer or anti-tumor agent.

2. Description of the Prior Art

Rapamycin is an antifungal antibiotic described by C. Vezina et al., J. Antibiot., 28, 721 (1975), S. N. Sehgal et al., J. Antibiot., 28, 727 (1975) and S. N. Sehgal et al., U.S. Pat. No. 3,929,992, issued Dec. 30, 1975, filed Apr. 12, 1974. Rapamycin is extracted from a streptomycete (Streptomyces hygroscopicus) isolated from an Easter Island soil sample and is particularly effective against Candida albicans both in vitro and in vivo.

In addition, a recent report by R. R. Martel et al., Can. J. Physiol., 55, 48 (1977) describes the use of rapamycin for the prevention of the development of two experimental immunopathies [(experimental allergic encephalomyelitis (EAE) and adjuvant arthritis (AA)]. The latter report also describes the inhibitory effect of rapamycin on the formation of humoral (IgE-like) antibody. This report concludes that immunosuppressant activity of rapamycin appears to be related to inhibition of the lymphatic system.

SUMMARY OF THE INVENTION

According to this invention a method is provided for treating carcinogenic tumors in a mammal which comprises administering to the mammal an antitumor effective amount of rapamycin. More specifically, rapamycin reduces tumor size in and prolongs the survival time of tumor bearing mammals.

DETAILS OF THE INVENTION

According to the present method, rapamycin is employed as the active agent. The isolation and description of rapamycin is given in U.S. Pat. No. 3,929,992, cited above, herein incorporated by reference.

Rapamycin is administered to a carcinogenic tumor bearing mammal for the purpose of reducing the tumor size and prolonging the survival time of the tumor bearing mammal, either orally or parenterally.

While rapamycin can be administered above, e.g. as a sole component of a filled capsule, it is preferred to formulate the compound in various dosage forms for oral or parenteral administration, e.g. tablets or sterile solutions. Such formulations are described in U.S. Pat. No. 3,929,992, cited above. Rapamycin may also be administered in combination with a therapeutically effective amount of an antineoplastic agent commonly used in cancer therapy.

When the antifungal antibiotic of this invention is employed as an anticancer agent in warm-blooded animals, e.g. rats, it may be used alone or in combination with a therapeutically effective amount of an antineoplastic agent commonly used in cancer therapy and with pharmaceutically acceptable carriers, the proportion of which is determined by the solubility and chemical nature of the compounds, chosen route of administration and standard biological practice. For example, an anticancer effective amount of the antibiotic may be administered alone or in combination orally in solid form containing such excipients as starch, sugar, certain types of clay and so forth. Similarly, such an amount may also be administered orally in the form of solutions or suspensions, or the antibiotic may be injected parenterally alone or in combination. For parenteral administration the antibiotic may be used alone or in combination in the form of a sterile solution or suspension containing other solutes or suspending agents, for example, enough saline or glucose to make the solution isotonic, bile salts, acacia, gelatin, sorbitan monooleate, polysorbate 80 (oleate esters of sorbitol and its anhydrides copolymerized with ethylene oxide) and the like.

When utilizing rapamycin alone or in combination with a therapeutically effective amount of an antineoplastic agent commonly used in cancer therapy for the treatment of tumors, the total dose of active agent can range from 0.5 to 500 mg per kg of body weight per day with a preferred dosage range from 10 to 250 mg per kg of body weight per day. However, as the dosage of rapamycin to be administered by the method of this invention will of course vary with the tumor or cancer and tolerance of the mammal, and with the nature of the other antineoplastic agents used in combination, it is preferred to initiate treatment of the tumor bearing mammal with a low daily dose of rapamycin and then to gradually increase the dosage until a desirable reduction in tumor size is achieved without causing any harmful or deleterious side effects. The schedule of dosing can range from one to five times per day to a single dose given every two to ten days. Such dosages and scheduling of administration must be determined on an individual basis, depending upon the tumor or cancer, nutritional state of the mammal, age of the mammal, toxicity in each individual, and with the nature of the other antineoplastic agents used in combination, etc.

Rapamycin reduces tumor size in and prolongs the survival time of tumorbearing mammals. More specifically, rapamycin is useful for controlling the following carcinogenic tumors in a mammal: lymphatic leukemia, colon, mammary, melanocarcinoma and ependymoblastoma. The effectiveness of rapamycin in this respect can be demonstrated in the laboratory with rodents having transplanted tumors. Details of methods used to evaluate this effect are described in various publications; for example, R. I. Geran et al., Cancer Chemother. Rep., Part 3, 3, (No. 2) 1–103 (1972) and references therein. In addition, the protocols for the antitumor tests are available from the National Cancer Institute, Bethesda, Md., U.S.A.

Tables 1 to 6 show the effects of therapy with rapamycin on various tumors or cancers in rodents.

More specifically, Table 1 shows the prolongation of survival time of female $CDF_1$ mice implanted with lymphatic leukemia P338 by administering rapamycin; Table 2 shows the reduction in size of colon 38 tumors in female $BDF_1$ mice by administering rapamycin; Table 3 shows the prolongation of survival time of male $CDF_1$ mice implanted with colon 26 tumors by administering rapamycin; Table 4 shows the reduction in size of $CD8F_1$ mammary tumors in male $CD8F_1$ rats by administering rapamycin; Table 5 shows the prolongation of survival time of female BDF₁ mice implanted with B16 melonocarcinoma by administering rapamycin; and Table 6 shows the prolongation of survival time of male Swiss mice implanted with ependymoblastoma by administering rapamycin.

TABLE 1

Effect of Rapamycin on Survival Time of CDF$_1$ Mice Implanted with Lymphatic Leukemia P-338 (ascetic)

| Dose/Inj. mg/kg | Ave. Wt. Difference of Animals (T − C, g) | Survivors on Day 5 | MST days T | MST days C | T/C % MST |
|---|---|---|---|---|---|
| 400 | −1.9 | 6/6 | 14.1 | 10.2 | 138 |
| 200 | −2.4 | 6/6 | 13.1 | 10.2 | 128 |
| 100 | −1.6 | 6/6 | 13.7 | 10.2 | 134 |
| 50 | −1.9 | 6/6 | 14.3 | 10.2 | 140 |
| 25 | −1.6 | 6/6 | 13.9 | 10.2 | 136 |
| 12.5 | −0.6 | 6/6 | 13.9 | 10.2 | 136 |

Treatment: Nine intraperitoneal injections starting on day one in a vehicle of saline with Tween-80 [Trade Mark for a derivative of Z-sorbitan mono-9-octadecenoate poly(oxy-1.2-ethanediyl)].
Evaluation: T/C % = Median Survival Time (MST) in days of treated animals (T)/control animals (C) × 100. A T/C % of 125 or greater is considered as a significant prolongation of host survival. Evaluation done on day 30.

TABLE 2

Effect of Rapamycin on Colon 38 Tumor Weight in Mice

| Dose/Inj. mg/kg | Ave. Wt. Difference of Animals (T − C, g) | Survivors on Day 5 | MTW mg T | MTW mg C | T/C % MTW |
|---|---|---|---|---|---|
| 400 | −3.4 | 10/10 | 188 | 810 | 23 |
| 200 | −2.0 | 10/10 | 209 | 810 | 25 |
| 100 | −0.8 | 10/10 | 272 | 810 | 33 |
| 50 | −0.8 | 9/10 | 320 | 810 | 39 |
| 25 | −0.4 | 10/10 | 368 | 810 | 45 |
| 12.5 | 0.4 | 10/10 | 368 | 810 | 45 |

Treatment: Single intraperitoneal injection on days 2, 9 and 16 in a vehicle of saline with Tween-80.
Evaluation: T/C % = Median tumor weight (MTW) estimated from tumor diameter of treated animals (T)/control animals (C) × 100. A T/C % of 42 or less is considered as a significant inhibitor of tumor growth. Evaluation done on day 20.

TABLE 3

Effect of Rapamycin on Survival Time of CDF$_1$ Mice Implanted with Colon 26 Tumor

| Dose/Inj. mg/kg | Ave. Wt. Difference of Animals (T − C, g) | Survivors on Day 5 | MST days T | MST days C | T/C % MST |
|---|---|---|---|---|---|
| 400 | −2.4 | 10/10 | 26.3 | 19.1 | 137 |
| 200 | −1.8 | 10/10 | 25.8 | 19.1 | 135 |
| 100 | −1.4 | 10/10 | 29.0 | 19.1 | 151 |
| 50 | −0.8 | 10/10 | 30.6 | 19.1 | 160 |
| 25 | −0.3 | 10/10 | 30.3 | 19.1 | 158 |
| 12.5 | 0.3 | 10/10 | 30.4 | 19.1 | 159 |

Treatment: Single intraperitoneal injection on days 1, 5 and 9 in a vehicle of saline with Tween-80.
Evaluation: T/C % = Median survival time (MST) in days of treated animals (T)/control animals (C) × 100. A T/C % of 125 or greater is considered as a significant prolongation of host survival. Evaluation done on day 60.

TABLE 4

Effect of Rapamycin on CD8F$_1$ Mammary Tumors in CD8F$_1$ Rats

| Dose/Inj. mg/kg | Average Net Wt. Difference of Animals (T − C, g) | Survivors on Day 5 | MTW mg T | MTW mg C | T/C % MTW |
|---|---|---|---|---|---|
| 400 | −6.6 | 4/10 | 0 | 3200 | — |
| 200 | −6.5 | 10/10 | 323 | 3200 | 10 |
| 100 | −4.8 | 10/10 | 448 | 3200 | 14 |
| 50 | −4.1 | 10/10 | 755 | 3200 | 23 |
| 25 | −2.4 | 10/10 | 825 | 3200 | 25 |
| 12.5 | −0.8 | 10/10 | 928 | 3200 | 29 |

Treatment: Single intraperitoneal injection on days 1, 8, 15, 22 and 29 in a vehicle of saline with Tween-80.
Evaluation: T/C % = Median tumor weight (MTW) estimated from tumor diameter of treated animals (T)/control animals (C) × 100. A T/C % of 42 or less is considered as a significant inhibitor of tumor growth. Evaluation done on day 30.

TABLE 5

Effect of Rapamycin on B16 Melanocarcinoma in BDF$_1$ Mice

| Dose/Inj. mg/kg | Average Net Wt. Difference of Animals (T − C, g) | Survivors on Day 5 | MST days T | MST days C | T/C % MST |
|---|---|---|---|---|---|
| 400 | −3.3 | 10/10 | 22.0 | 20.1 | 109 |
| 200 | −1.5 | 10/10 | 22.3 | 20.1 | 110 |
| 100 | −1.2 | 10/10 | 28.0 | 20.1 | 139 |
| 50 | −0.7 | 10/10 | 25.3 | 20.1 | 125 |
| 25 | 0.1 | 10/10 | 28.0 | 20.1 | 139 |
| 12.5 | 0.1 | 10/10 | 29.0 | 20.1 | 144 |

Treatment: Single intraperitoneal injection on each of days 1 through 9 in a vehicle of saline with Tween-80.
Evaluation: T/C % = Median Survival Time (MST) in days of treated animals (T) control animals (C) × 100. A T/C % of 125 or greater is considered as a significant prolongation of host survival. Evaluation done on day 60.

TABLE 6

Effect of Rapamycin on Ependymoblastoma in Swiss Mice

| Dose/Inj. mg/kg | Average Net Wt. Difference of Animals (T − C, g) | Survivors on Day 5 | MST days T | MST days C | T/C % MST |
|---|---|---|---|---|---|
| 200 | −3.3 | 10/10 | 44.0 | 18.1 | 243 |
| 100 | −2.2 | 10/10 | 26.0 | 18.1 | 143 |
| 50 | −1.3 | 9/10 | 34.0 | 18.1 | 187 |
| 25 | −2.0 | 10/10 | 34.0 | 18.1 | 187 |
| 12.5 | −1.0 | 10/10 | 32.3 | 18.1 | 178 |

Treatment: Single intraperitoneal injection on each of days 1 through 9 in a vehicle of saline with Tween-80.
Evaluation: T/C % = Median Survival Time (MST) in days of treated animals (T) control animals (C) × 100. A T/C % of 125 or greater is considered as a significant prolongation of host survival. Evaluation done on day 60.

Rapamycin also can be used to produce beneficial effects in the treatment of malignant tumors when combined with a therapeutically effective amount of an antineoplastic agent commonly used in cancer therapy. Such antineoplastic agents include the alkylating agents, for example, busulfan, chlorambucil, cyclophosphamide, mechlorethamine hydrochloride, melphalan, pipobroman, thiotepa and uracil mustard; antimetabolites, for example, cytarabine, fluorouracil, floxuridine, mercaptopurine, methotrexate and thioguanine; miscellaneous anticancer agents, for example, dacarbazine, hydroxyurea, mitotane, procarbazine hydrochloride, quinacrine hydrochloride, vinblastine sulfate and vincristine sulfate; estogens, for example, chlorotrianisene, conjugate estogens (e.g. PREMARIN ®), diethylstilbestrol and the like; androgens, for example, methyltestosterone, testosterone and the like; adrenal corticosteroids, for example, prednisone and the like; progestagens, for example, megestrol, hydroxyprogesterone caproate and the like; radioactive isotopes; and antibiotics, for example, bleomycin sulfate, doxorubicin hydrochloride and the like. Suitable methods of administration, compositions and dosages of the antineoplastic agents are described in medical textbooks; for instance, "PHYSICIANS' DESK REFERENCE", 32nd ed., Medical Economics Co., Oradell, N.J., U.S.A., 1978 and "AMA DRUG EVALUATIONS", 3rd ed. PSG Publishing Company, Inc., Littleton, Mass., U.S.A. pp 1106–1151, 1977. When used in combination, rapamycin is administered as described previously; however, a lower dose can be used for efficacious results.

We claim:

1. A method of treating colon tumors in a mammal, which comprises administering to said mammal an antitumor effective amount of rapamycin in combination with an antitumor effective amount of the antineoplastic agents 5-fluorouracil and cyclophosphamide.

2. The method of claim 1 wherein rapamycin and said antineoplastic agents are administered sequentially.

3. The method of reducing tumor size in a colon tumor bearing mammal, comprising administering to said mammal an anti-colon tumor effective amount of rapamycin in combination with an antitumor effective amount of the antineoplastic agents 5-fluorouracil and cyclophosphamide.

4. The method of prolonging the survival time of a colon tumor bearing mammal, which comprises administering to said mammal an anti-colon tumor effective amount of rapamycin in combination with an antitumor effective amount of the antineoplastic agents 5-fluorouracil and cyclophosphamide.

5. The method of claim 1 wherein rapamycin is administered at a dose of 0.5 to 500 mg per kg of body weight.

6. The method of claim 1 wherein rapamycin is administered at a dose of 10 to 250 mg per kg of body weight.

* * * * *

UNITED STATES PATENT AND TRADEMARK OFFICE
CERTIFICATE OF CORRECTION

PATENT NO. : 5,066,493
DATED : November 19, 1991
INVENTOR(S) : Surendra N. Sehgal
Claude Vezina It is certified that error appears in the above-identified patent and that said Letters Patent is hereby corrected as shown below:

On title page, item [73]

Should read:

[73] Assignee: Ayerst, McKenna & Harrison, Inc.
St. Laurent, Quebec, Canada

Signed and Sealed this

Ninth Day of March, 1993

*Attest:*

STEPHEN G. KUNIN

*Attesting Officer*   *Acting Commissioner of Patents and Trademarks*